United States Patent
Harmsen et al.

(10) Patent No.: US 7,453,014 B2
(45) Date of Patent: Nov. 18, 2008

(54) PROCESS FOR THE PREPARATION OF ALKYLENE GLYCOL

(75) Inventors: Gerrit Jan Harmsen, Amsterdam (NL); Arthur Willibrordus Titus Rots, Amsterdam (NL); Anton Pieter Westerink, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/949,592

(22) Filed: Dec. 3, 2007

(65) Prior Publication Data

US 2008/0154070 A1      Jun. 26, 2008

(30) Foreign Application Priority Data

Dec. 4, 2006      (EP) .................................. 06256180

(51) Int. Cl.
*C07C 29/09*      (2006.01)
*C07C 27/00*      (2006.01)
*C07C 31/30*      (2006.01)

(52) U.S. Cl. ........................ 568/858; 568/852; 568/857

(58) Field of Classification Search ................. 568/858, 568/857, 852

See application file for complete search history.

(56) References Cited

U.S. PATENT DOCUMENTS

| 4,283,580 | A | 8/1981 | Odanaka et al. .............. 568/858 |
| 5,231,212 | A | 7/1993 | Buysch et al. .............. 558/277 |
| 6,080,897 | A | 6/2000 | Kawabe ...................... 568/858 |
| 6,187,972 | B1 | 2/2001 | Kawabe et al. .............. 568/858 |

*Primary Examiner*—Elvis O Price

(57) ABSTRACT

The invention provides a process for the preparation of an alkaline glycol from an alkaline carbonate, wherein alkaline carbonate is hydrolyzed in the presence of catalyst in a baffled reactor. The baffled reactor has at least four compartments, the compartments are formed by internal baffles and the internal baffles provide a sinuous route for reaction fluid through the reactor.

20 Claims, 3 Drawing Sheets

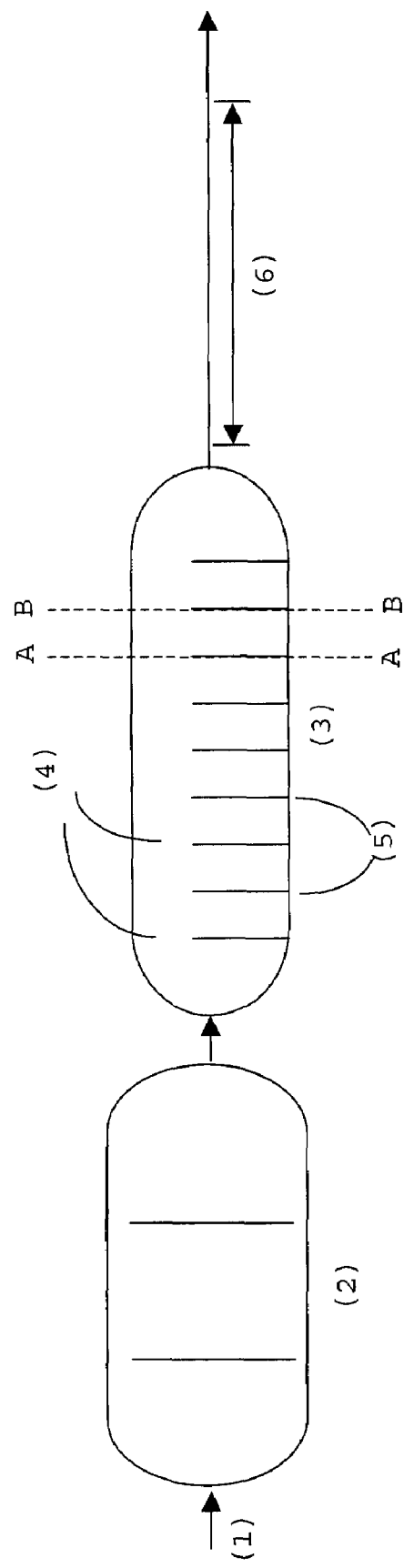
FIGURE 3A
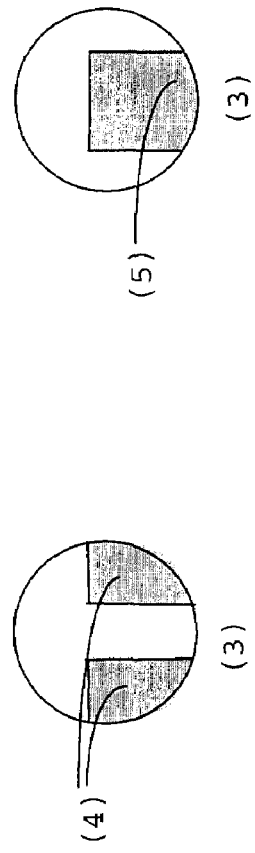
FIGURE 3B
FIGURE 3C

PROCESS FOR THE PREPARATION OF ALKYLENE GLYCOL

CROSS-REFERENCE TO RELATED APPLICATIONS

This application claims the benefit of European Patent Application No. 06256180.8, filed Dec. 4, 2006, which is incorporated herein by reference in its entirety.

FIELD OF THE INVENTION

The present invention relates to a process for the preparation of an alkylene glycol wherein an alkylene carbonate undergoes hydrolysis in the presence of a catalyst.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol may be prepared from ethylene oxide via ethylene carbonate. This is typically carried out in a two-step process wherein the first step is the reaction of ethylene oxide with carbon dioxide to form ethylene carbonate, and the second step is the hydrolysis of ethylene carbonate to form ethylene glycol.

U.S. Pat. No. 6,187,972 describes a process for manufacturing ethylene glycol from ethylene carbonate wherein the hydrolysis is carried out in two reactors. In an example, the conversion of ethylene carbonate achieved in the first reactor is 93.0% and in the second reactor is about 100% (the detection limit was less than 10 ppm). It is desirable to minimise the amount of unreacted ethylene carbonate that remains in the ethylene glycol product because the compounds form an azeotropic mixture and their separation and purification is difficult. A similar process for manufacturing ethylene glycol is disclosed in U.S. Pat. No. 6,080,897.

The present inventors have sought to further improve the manufacture of alkylene glycol from alkylene carbonate, maximising conversion and minimising liquid shortcutting whilst ensuring that the process is as economical as possible. In practice, decreasing the residence time of the reactants and/or decreasing the reactor size can increase the economy (i.e. minimise the cost) of the process. The present inventors have therefore sought to provide an improved process wherein the conversion to alkylene glycol is maximised (and is preferably 100%) and liquid shortcutting is avoided whilst maintaining or decreasing the residence time and/or the reactor size.

SUMMARY OF THE INVENTION

Accordingly, the present invention provides a process for the preparation of an alkylene glycol from an alkylene carbonate, which comprises hydrolyzing alkylene carbonate in the presence of catalyst in a baffled reactor, wherein the baffled reactor has at least four compartments, the compartments are formed by internal baffles and the internal baffles provide a sinuous route for reaction fluid through the reactor.

The process of the invention provides excellent conversion of an alkylene carbonate to an alkylene glycol. The inventors have found that using the baffled reactor reduces variation in residence time and prevents shortcutting of liquid, so the likelihood of any alkylene carbonate molecule passing through the reactor quickly and without reacting is minimised and the likelihood of any molecule remaining in the reactor for an extended period (in a so-called dead zone in the reactor) is also minimised. The conversion to alkylene glycol can be maximised whilst minimising the residence time and/or reactor size.

BRIEF DESCRIPTION OF THE DRAWINGS

FIG. 3 is a schematic diagram showing a process according to a yet further embodiment of the invention.

DETAILED DESCRIPTION OF THE INVENTION

Figure 1A:
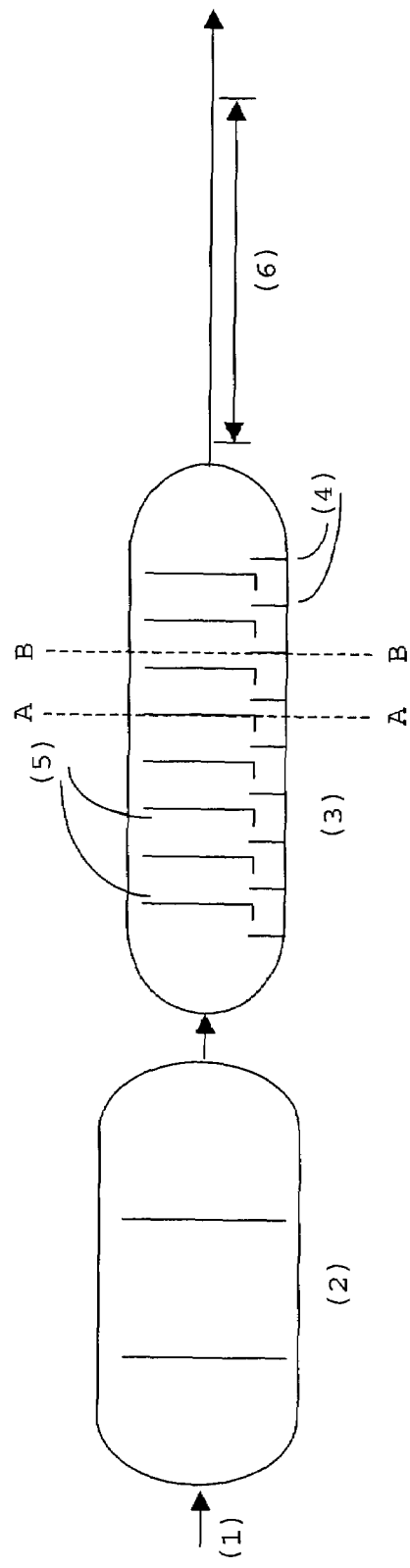
FIG. 1 is a schematic diagram showing a process according to an embodiment of the invention.

The present invention provides a process for the preparation of an alkylene glycol from an alkylene carbonate:

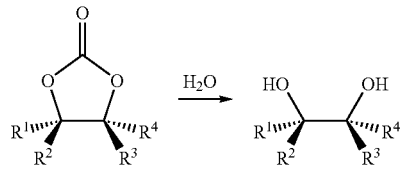

$R^1$, $R^2$, $R^3$ and $R^4$ may independently be chosen from hydrogen or an optionally substituted alkyl group having from 1 to 6 carbon atoms, preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkylene carbonates therefore include ethylene carbonate and propylene carbonate. In the present invention, the most preferred alkylene carbonate is ethylene carbonate.

The baffled reactor has at least four compartments.

The term "compartment" is used to describe a subdivision of the volume of a reactor through which the reaction fluids must pass, e.g. if the reactor has two compartments, reaction fluids must travel through both compartments before exiting the reactor. Preferably the baffled reactor has at least six compartments, most preferably at least ten compartments. Increased numbers of compartments decreases the variability of residence time and therefore increases the conversion of alkylene carbonate to alkylene glycol for a given reactor volume or can maintain the conversion level with a smaller reactor volume.

The reaction fluid is a liquid phase and is present in the reactor below a gaseous phase.

It is preferred that the reaction fluids pass from compartment to compartment without leaving the reactor, i.e. there are no external pipes connecting the compartments.

The dimensions of the reactor are preferably such that, in use, the reactor is longer in the horizontal dimension than it is in the vertical dimension. Preferably, one or more inlets for reactants are positioned at one side of the reactor and one or more outlets for products are positioned at another side of the reactor, i.e. the reaction fluid travels from one side of the reactor to another side, rather than from top to bottom, or bottom to top.

The compartments in each reactor are formed by internal baffles and the internal baffles provide a sinuous route for reaction fluid through the reactor. The term "sinuous route" is used to describe an undulating route through the reactor (e.g. an up-down-up-down route or a left-right-left-right route). However a "sinuous route" does not mean that all molecules follow a smooth, direct sinuous route through the reactor; instead it is preferred that the majority of molecules follow a highly disrupted route through the reactor, deviating from a smooth sinuous route that represents the net flow. Preferably, the sinuous route through the reactor is substantially horizontal, i.e. the route is from one side of the reactor to another side, even if the undulations are up-down.

The term "internal baffle" is used to describe a plate that is present within the reactor, subdividing the reactor volume into compartments and disrupting the flow of reaction fluids. The baffles optionally contain a plurality of holes through which the reaction fluid can pass, but preferably do not contain holes. The baffles may conveniently extend from one internal surface of the reactor or may connect two internal surfaces of the reactor. The smallest angle at the interface between the surface of baffle and the internal surface of the reactor is preferably greater than 45°, more preferably greater than 60°. Most preferably, the baffles are perpendicular to the internal surface of the reactor.

The baffles are preferably selected from downwardly extending baffles; upwardly extending baffles; baffles extending from one side of the reactor to the other; and mixtures thereof. The terms "upwardly", "downwardly" and "from one side to the other" denote directions in the reactor when the reactor is used in the process of the invention. The terms are not used to describe only directions that are exactly perpendicular to the internal surfaces of the reactor, but also denote directions that are up to 45° from the perpendicular, preferably up to 30° from the perpendicular (e.g. an upwardly extending baffle extends upwards from the bottom surface of the reactor, but the angle formed between the bottom surface and the surface of the baffle is from 90° to 45°).

In a preferred embodiment, the compartments in the baffled reactor are formed by a series of alternating first internal baffles and second internal baffles that provide a sinuous route for reaction fluid through the reactor.

In a most preferred embodiment the reaction fluids pass over the first internal baffles and reaction fluids pass under the second internal baffles. For example, the first internal baffles may be upwardly extending baffles and the second internal baffles may be baffles extending from side-to-side of the reactor. (The second internal baffles may be downwardly extending baffles but this is not preferred because gas flow over the top of the baffle is prevented.) The reaction fluids flow over the top of the upwardly extending baffles and flow underneath the side-to-side baffles.

Preferably, the top edges of the first internal baffles are higher than the bottom edges of the second internal baffles. ("Higher" means closer to the top of the reactor when the reactor is used in the process of the invention.) This means that there is overlap of the baffles and the reaction fluid follows a sinuous route over the top edges of the first internal baffles and underneath the bottom edges of the second internal baffles. Most preferably, the angle between a line from the top edge of the first internal baffle to the bottom edge of the second internal baffle and the horizontal is in the range of from 5 to 15°.

Preferably, the second internal baffles have a "lip", i.e. there are extended sections at the bottom edges of the second internal baffles. The lip is preferably horizontal or up to 30° from the horizontal. (The term "horizontally" denotes a direction in the reactor when the reactor is used in the process of the invention.) The provision of the lip on the second internal baffles increases mixing as the liquids pass from one compartment in the reactor to the next and at the same time prevents shortcutting of liquid by providing a disrupted sinuous route for reaction fluids through the reactor.

In a further preferred embodiment, the reaction fluids pass around one side (e.g. the left) of the first internal baffles and reaction fluids pass around the other side (e.g. the right) of the second internal baffles. For example, the first internal baffles may extend from a first side (e.g. the right) of the reactor and the second internal baffles may extend from a second side (e.g. the left) of the reactor. The reaction fluids flow around the left hand side of the first internal baffles and flow around the right hand side of the second internal baffles. Preferably, there is overlap of the first internal baffles and second internal baffles.

In a yet further preferred embodiment, the reaction fluids pass between a pair of first internal baffles and then around both sides of the second internal baffles. For example, the first internal baffles may extend from both sides of the reactor and the second internal baffles may be upwardly extending baffles. The reaction fluids flow between the pair of first internal baffles and then around both sides of the upwardly extending baffle.

Steam may be injected into the baffled reactor. Steam injection can increase turbulence and disrupt the sinuous flow pattern of the liquid and can therefore also be used to decrease the variability in residence time and prevent liquid shortcutting. Preferably, steam is injected into at least every second compartment, and most preferably, steam is injected into every compartment. In the embodiment of the invention wherein the reaction fluids pass over the first internal baffles and reaction fluids pass under the second internal baffles, steam is preferably injected below the second internal baffles.

Mechanical stirring may be used in the baffled reactor, but this is not preferred because it increases the complexity of the reactor and is generally unnecessary as sufficient mixing is provided by the baffled structure and can be provided by optional steam addition.

Hydrolysis of the alkylene carbonate takes place in the baffled reactor in the presence of catalyst. Suitable catalysts are known to the skilled person and are described, for example, in U.S. Pat. No. 4,283,580. Preferred catalysts include a carbonate of an alkali metal such as potassium carbonate or a molybdate such as potassium molybdate. The catalyst is supplied to the baffled reactor with the reactants.

The temperature in the baffled reactor is typically from 80 to 200° C., preferably from 100 to 180° C. The pressure in the baffled reactor is typically from 0.1 to 3 MPa, preferably from 0.1 to 2 MPa and most preferably from 0.2 to 1 MPa.

In a preferred embodiment of the invention, the process comprises hydrolyzing alkylene carbonate in the presence of catalyst in a first reactor and in the baffled reactor, wherein the baffled reactor is downstream of the first reactor, wherein the first reactor has one or more compartments and wherein the baffled reactor has more compartments than the first reactor.

The first reactor and the baffled reactor are arranged in series (the baffled reactor is downstream of the first reactor), such that reactants are supplied to the first reactor, wherein hydrolysis of a proportion of the alkylene carbonate will occur, and the product stream from the first reactor is then passed (optionally but not preferably via further reactors) to the baffled reactor wherein further hydrolysis of remaining alkylene carbonate will occur. In a preferred embodiment of the invention, hydrolysis of alkylene carbonate in the presence of catalyst takes place only in two reactors (the first reactor and the baffled reactor) and the baffled reactor is directly downstream of the first reactor, i.e. alkylene carbonate is supplied to the first reactor (preferably as a component of a product stream from a carboxylation reactor), hydrolysis occurs in the first reactor, the product stream is passed directly to the baffled reactor wherein hydrolysis of remaining alkylene carbonate occurs, and a product stream comprising alkylene glycol (and preferably less than 1 wt % alkylene carbonate, most preferably 0% alkylene carbonate) emerges from the baffled reactor. It is preferred that hydrolysis occurs in two reactors because this is a simple and economical system design yet high conversions can be achieved. In an alternative embodiment of the invention, hydrolysis of alkylene carbonate in the presence of catalyst takes place in three or more reactors (preferably three to five) arranged in series or in parallel (although the baffled reactor must be downstream of the first reactor). One of the reactors is the first reactor of the invention, and one of the reactors, downstream of the first reactor, is the baffled reactor of the invention. Preferably, the final reactor in the series of reactors is a baffled reactor. The hydrolysis may also occur in more than one baffled reactor with the preferred features as described above, for example in a series of three reactors there may be a first reactor and two baffled reactors downstream of the first reactor.

The first reactor preferably has from one to three compartments and most preferably has three compartments. The first reactor can have a relatively simple design because it is not important to minimise the amount of alkylene carbonate that emerges from the first reactor because the liquids will subsequently be passed to the baffled reactor and undergo further reaction.

Preferably, the pressure in the first reactor is higher than the pressure in the baffled reactor. High pressure is preferred in the first reactor because the cost of recycling carbon dioxide is lower. Lower pressure in the baffled reactor is desirable because this increases the reaction rate (at least for catalyst systems such as potassium carbonate). The pressure in the first reactor is typically from 0.2 to 5 MPa, preferably from 0.5 to 3 MPa and most preferably from 1 to 2.5 MPa.

The temperature in the first reactor is typically from 80 to 200° C., preferably from 100 to 180° C.

In a preferred embodiment of the invention, an outlet tube having a high length to diameter ratio is connected to the baffled reactor. Preferably, the residence time of the product stream in this outlet tube is at least 20 seconds, more preferably at least 30 seconds. An outlet tube of this type can be used to further increase the conversion to alkylene glycol because any remaining alkylene carbonate is likely to undergo hydrolysis whilst in the outlet tube.

The product stream from the baffled reactor (or the product stream from an outlet tube connected to the baffled reactor) contains alkylene glycol and preferably contains less than 10 ppm alkylene carbonate, most preferably no detectable alkylene carbonate. The alkylene glycol-rich product stream is typically subjected to distillation to obtain a dehydrated alkylene glycol and a solution of the hydrolysis catalyst. The hydrolysis catalyst is supplied as a catalyst solution to the reactant stream that is provided to the first reactor.

FIG. 1a shows a process according to an embodiment of the invention. A reactant stream (1) of ethylene carbonate, water and catalyst is fed into a first reactor (2). In the first reactor, ethylene carbonate is hydrolysed to give ethylene glycol. The first reactor is partitioned into three compartments. The product stream from the first reactor containing ethylene glycol, any unreacted water and ethylene carbonate, and catalyst is fed to a baffled reactor (3). The baffled reactor (3) is partitioned into compartments by alternating first internal baffles and second internal baffles (4, 5). The first internal baffles (4) are upwardly extending baffles and the second internal baffles (5) are side-to-side baffles. The side-to-side baffles (5) have a horizontally-extending lip section at the bottom edge of the plate.

Figure 1D:
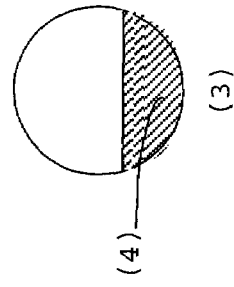
Figure 1C:
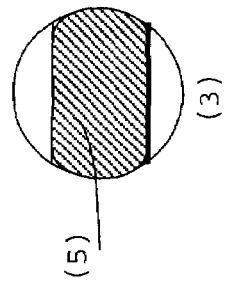
Figure 1B:
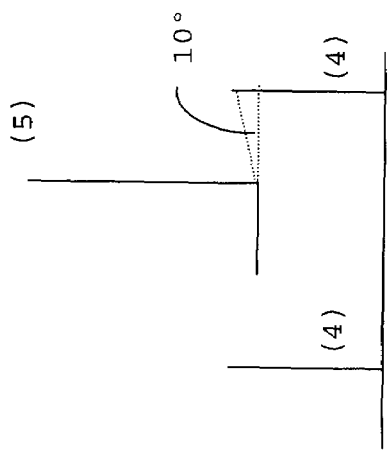

The positioning of the baffles (4, 5) is shown further in FIGS. 1b, 1c and 1d. FIG. 1b shows that the angle between a line from the bottom edge of the second internal baffle (4) to the top edge of the first internal baffle (5) and the horizontal is 10° (figure is not drawn to scale). FIG. 1c is a cross-section of FIG. 1a taken through line A-A and showing a second internal baffle (5) in the baffled reactor (3). The second internal baffles (5) extend between the sides of the baffled reactor (3) but do not extend to the top and bottom of the reactor. FIG. 1d is a cross-section of FIG. 1a taken through line B-B and showing a first internal baffle (4) in the baffled reactor (3). The first internal baffle (4) extends upwards from the base of the reactor (3).

FIG. 1a also shows an outlet tube connected to the baffled reactor (3). The liquids in the baffled reactor (3) have a disrupted sinuous route through the reactor and it is likely that all remaining ethylene carbonate will be hydrolysed in the baffled reactor (3). If any ethylene carbonate does emerge from the baffled reactor (3), it is likely be hydrolysed in the outlet tube. The residence time of the liquids in the portion of the outlet tube indicated by (6) is at least 20 seconds. The liquids pass from the outlet tube to a dehydrator where the ethylene glycol is distilled.

Figure 2A:
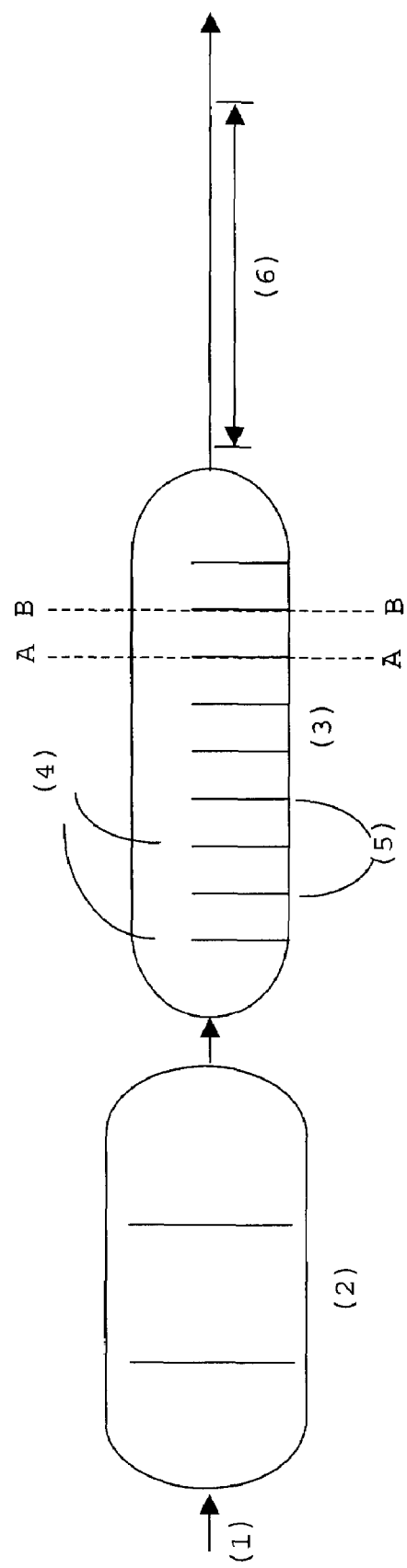
FIG. 2 is a schematic diagram showing a process according to a further embodiment of the invention.

FIG. 2a shows a process according to a further embodiment of the invention. The features of the process are the same as those shown in FIG. 1a except for the configuration of the first internal baffles and second internal baffles (4, 5). The first internal baffles (4) extend from one side of the reactor and the second internal baffles (5) extend from the other side of the reactor.

Figure 2B:
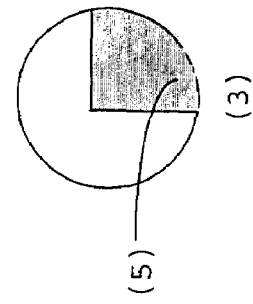
Figure 2C:
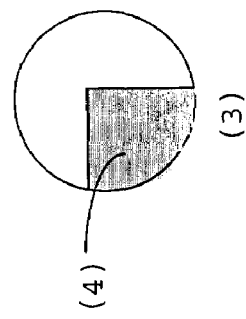

The positioning of the baffles (4, 5) is shown further in FIGS. 2b and 2c. FIG. 2b is a cross-section of FIG. 2a taken through line A-A and showing a first internal baffle (4) in the baffled reactor (3). The first internal baffle (4) extends from one side of the baffled reactor (3), extending to the bottom but not the top of the reactor. FIG. 2c is a cross-section of FIG. 2a taken through line B-B and showing a second internal baffle (5) in the baffled reactor (3). The second internal baffle (5) extends from the other side of the baffled reactor (3), extending to the bottom but not the top of the reactor. The liquids in the baffled reactor (3) flow around the sides of the first and second internal baffles (4, 5) and it is likely that all remaining ethylene carbonate will be hydrolysed in the baffled reactor (3).

FIG. 3a shows a process according to a yet further embodiment of the invention. The features of the process are the same as those shown in FIG. 1a except for the configuration of the first internal baffles and second internal baffles (4, 5). The first internal baffles (4) extend from both sides of the reactor and the second internal baffles (5) are upwardly-extending baffles.

The positioning of the baffles (4, 5) is shown further in FIGS. 3b and 3c. FIG. 3b is a cross-section of FIG. 3a taken through line A-A and showing a first internal baffle (4) in the baffled reactor (3). The first internal baffles (4) extend from both side of the baffled reactor (3), extending to the bottom but not the top of the reactor and providing a path for reaction fluid between the opposing pair of baffles. FIG. 3c is a cross-section of FIG. 3a taken through line B-B and showing a second internal baffle (5) in the baffled reactor (3). The second internal baffle (5) extends from the bottom of the baffled reactor (3), but does not extend to the sides or the top of the reactor. The liquids in the baffled reactor (3) flow between the first internal baffles (4) and around both sides of the second internal baffles (5) and it is likely that all remaining ethylene carbonate will be hydrolysed in the baffled reactor (3).

What is claimed is:

1. A process for the preparation of an alkaline glycol from an alkaline carbonate, which comprises hydrolyzing alkaline carbonate in the presence of a catalyst in a baffled reactor, wherein the baffled reactor has at least four compartments, the compartments are formed by internal baffles and the internal baffles provide a sinuous route for a reaction fluid through the reactor.

2. A process according to claim 1, wherein the baffled reactor has at least six compartments.

3. A process according to claim 1, wherein the baffled reactor has at least ten compartments.

4. A process according to claim 1, wherein the compartments in the baffled reactor are formed by a series of alternating first internal baffles and second internal baffles that provide the sinuous route for the reaction fluid through the reactor.

5. A process according to claim 4, wherein the reaction fluid passes over the first internal baffles and under the second internal baffles.

6. A process according to claim 5, wherein the top edges of the first internal baffles are higher than the bottom edges of the second internal baffles.

7. A process according to claim 6, wherein the angle between a line from the top edges of the first internal baffles to the bottom edges of the second internal baffles and the horizontal is in the range of from 5 to 15°.

8. A process according to claim 4, wherein the second internal baffles have extended sections at their bottom edges.

9. A process according to claim 4, wherein the first internal baffles are upwardly extending baffles and the second internal baffles extend from side-to-side of the reactor.

10. A process according to claim 4, wherein the first internal baffles extend from a first side of the reactor and the second internal baffles extend from a second side of the reactor.

11. A process according to claim 10, wherein the first internal baffles and the second internal baffles overlap.

12. A process according to claim 4 wherein the first internal baffles extend from both sides of the reactor such that the reaction fluid flows between the first internal baffles and the second internal baffles are upwardly extending baffles such that the reaction fluid flows around both sides of the second internal baffles.

13. A process according to claim 1, wherein steam is injected into at least one compartment in the baffled reactor.

14. A process according to claim 1, wherein steam is injected into every compartment in the baffled reactor.

15. A process according to claim 1, which comprises hydrolyzing alkaline carbonate in the presence of a catalyst in a first reactor and in the baffled reactor, wherein the baffled reactor is downstream of the first reactor, wherein the first reactor has one or more compartments, and wherein the baffled reactor has more compartments than the first reactor.

16. A process according to claim 15, wherein a product stream from the baffled reactor contains alkaline glycol and less than 10 ppm alkaline carbonate.

17. A process according to claim 15, comprising hydrolyzing alkaline carbonate in the presence of a catalyst in three or more reactors.

18. A process according to claim 15, wherein the pressure in the first reactor is higher than the pressure in the baffled reactor.

19. A process according to claim 1, wherein an outlet tube is connected to the baffled reactor and the residence time of a product stream in the outlet tube is at least 20 seconds.

20. A process according to claim 19, wherein the product stream from the outlet tube contains alkaline glycol and less than 10 ppm alkaline carbonate.

* * * * *